United States Patent
Chen

(10) Patent No.: US 9,649,934 B2
(45) Date of Patent: May 16, 2017

(54) DRIVING SAFETY CONTROLLING SYSTEM AND DRIVING SAFETY CONTROLLING METHOD USING SAME

(71) Applicant: HON HAI PRECISION INDUSTRY CO., LTD., New Taipei (TW)

(72) Inventor: Wei-An Chen, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 14/716,538

(22) Filed: May 19, 2015

(65) Prior Publication Data

US 2016/0189449 A1 Jun. 30, 2016

(30) Foreign Application Priority Data

Dec. 31, 2014 (TW) .............................. 103146681 A

(51) Int. Cl.
*G06F 1/16* (2006.01)
*G05B 1/03* (2006.01)
(Continued)

(52) U.S. Cl.
CPC ............ *B60K 28/06* (2013.01); *B60R 25/252* (2013.01); *B60W 50/14* (2013.01);
(Continued)

(58) Field of Classification Search
CPC ........ G07C 2009/0096; G07C 9/00563; G07C 9/00158; G07C 9/00111; G07C 9/00126; G07C 5/008; G07C 2009/00095; G07C 9/00087; B60R 25/25; B60R 2325/105; B60R 25/01; B60R 25/252; B60W 40/08; B60W 2040/0809; B60W 2040/0827; B60W 2040/0836; B60W 2040/0845; B60W 2040/0872; B60W 2040/089; G06K 2009/00939; G06K 9/00536; G06K 19/0718; G06K 17/0022; B60K 28/06;
(Continued)

(56) References Cited

U.S. PATENT DOCUMENTS

2004/0236701 A1* 11/2004 Beenau ............ G06F 17/30725
705/64
2006/0219776 A1* 10/2006 Finn ........................ B60R 25/25
235/380

(Continued)

*Primary Examiner* — Dionne H Pendleton
(74) *Attorney, Agent, or Firm* — Steven Reiss

(57) ABSTRACT

A driving safety controlling method is provided. The controlling method is running on a wearable device, a smart key and a vehicle. The control controlling method comprises steps: obtaining sensing data stored in a first storage unit of the wearable device; obtaining a unique identifier stored in a second storage unit of the smart key and controlling a first wireless communication unit of the smart key to transmit a high-frequency signal containing the unique identifier and the sensing data to the vehicle; obtaining a predefined identifier and a range from a third storage unit of the vehicle, comparing the unique identifier with the predefined identifier, and comparing the sensing data with the range; and controlling a prompt unit to generate a prompting when the unique identifier is determined to match with the predefined identifier and the sensing data is within the range.

10 Claims, 3 Drawing Sheets

(51) Int. Cl.
*B60K 28/06* (2006.01)
*G07C 9/00* (2006.01)
*B60R 25/25* (2013.01)
*B60W 50/14* (2012.01)
*B60W 40/08* (2012.01)

(52) U.S. Cl.
CPC ..... *G07C 9/00087* (2013.01); *G07C 9/00126* (2013.01); *G07C 9/00158* (2013.01); *B60W 2040/0872* (2013.01)

(58) Field of Classification Search
CPC ..... B60K 28/063; B60K 28/066; G06F 21/32; G06F 21/31; G06F 3/016; G06F 3/017
See application file for complete search history.

(56) References Cited

U.S. PATENT DOCUMENTS

| | | | | |
|---|---|---|---|---|
| 2009/0121833 | A1* | 5/2009 | Falck | G07C 9/00087 340/5.64 |
| 2014/0266597 | A1* | 9/2014 | Narendra | G05B 1/03 340/5.81 |
| 2014/0282931 | A1* | 9/2014 | Protopapas | G06F 21/31 726/5 |
| 2014/0309870 | A1* | 10/2014 | Ricci | H04W 48/04 701/36 |
| 2015/0220109 | A1* | 8/2015 | von Badinski | G01P 15/00 340/539.12 |
| 2016/0001781 | A1* | 1/2016 | Fung | G06F 19/345 701/36 |

* cited by examiner

DRIVING SAFETY CONTROLLING SYSTEM AND DRIVING SAFETY CONTROLLING METHOD USING SAME

FIELD

The subject matter herein generally relates to driving safety controlling systems and driving safety controlling methods using same.

BACKGROUND

The wearable devices, such as wearable glass, wearable watch, or the like, are welcome for more and more users. The wearable devices can be used to monitor the driving safety of the vehicle. However, the wearable devices cannot be matched with the vehicles accurately.

BRIEF DESCRIPTION OF THE DRAWINGS

Many aspects of the present disclosure are better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

Figure 1:
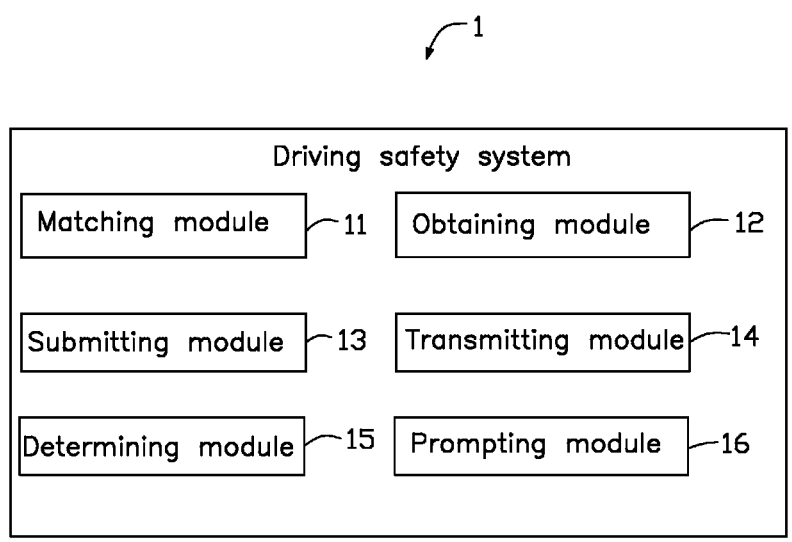
FIG. 1 is a block diagram of an embodiment of a driving safety controlling system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. Also, the description is not to be considered as limiting the scope of the embodiments described herein. The drawings are not necessarily to scale and the proportions of certain parts may be exaggerated to better illustrate details and features of the present disclosure.

A definition that applies throughout this disclosure will now be presented.

The term "comprising," when utilized, means "including, but not necessarily limited to"; it specifically indicates open-ended inclusion or membership in the so-described combination, group, series and the like.

Figure 2:
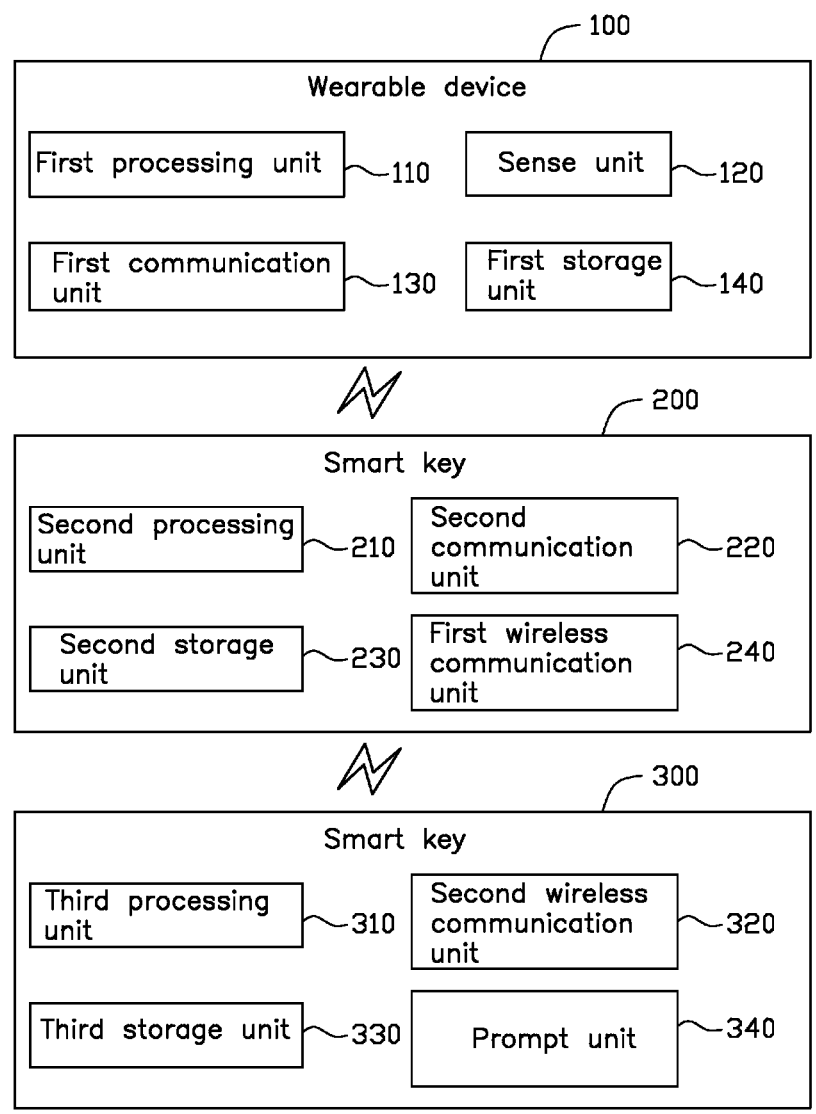
FIG. 2 is a block diagram of an embodiment of an operating environment of the driving safety controlling system shown in FIG. 1.

FIG. 1 shows a driving safety controlling system 1. The driving safety controlling system 1 can be run on but not limited to a wearable device 100, a smart key 200 and a vehicle 300 which are shown on FIG. 2.

The wearable device 100 can be but not limited to a wearable glass, a wearable watch, a wearable cloth, or the like. The wearable device 100 can include a first processing unit 110, a sense unit 120, a first communication unit 130 and a first storage unit 140.

The sense unit 120 can be located on many locations of the wearable device 100. The sense unit 120 can sense a user's physiological status, such as blood pressure, pulse rate, blink response, the number of eye-rolling or the like, and further generate a sensing data.

The first storage unit 140 can be used to store the sensing data.

The first communication unit 130 can be but not limited to Bluetooth, WiFi, RFID or other suitable communication device.

The smart key 200 can include a second processing unit 210, a second communication unit 220, a second storage unit 230 and a first wireless communication unit 240.

The second communication unit 220 can be but not limited to Bluetooth, WiFi, RFID or other suitable communication device. The second communication unit 220 and the first communication unit 130 can cooperatively establish a communication between the wearable device 100 and the smart key 200.

The second storage unit 230 can be used to store a unique identifier.

The first wireless communication unit 240 can be used to transmit a high-frequency signal containing the sensing data and the unique identifier.

The vehicle 300 can include a third processing unit 310, a second wireless communication unit 320, a third storage unit 330 and a prompt unit 340.

The third storage unit 330 can store a range recording a user's physiological status and a predefined identifier.

The second wireless communication unit 320 can be used to receive the high-frequency signal.

In at least one embodiment, the first storage unit 140, the second storage unit 230 and the third storage unit 330 can be an internal storage controlling system, such as a flash memory, a random access memory (RAM) for temporary storage of information, and/or a read-memory (ROM) for permanent storage of information.

In at least one embodiment, the first storage unit 140, the second storage unit 230 and the third storage unit 330 can also be a storage controlling system, such as a hard disk, a storage card, or a data storage medium. The first storage unit 140, the second storage unit 230 and the third storage unit 330 can include volatile and/or non-volatile storage devices.

In at least one embodiment, the first storage unit 140, the second storage unit 230 and the third storage unit 330 can include two or more storage devices such that one storage device is a memory and the other storage device is a hard drive. Additionally, the first storage unit 140, the second storage unit 230 and the third storage unit 330 can be respectively located either entirely or partially external relative to the wearable device 100, the smart key 200 or the vehicle 300.

In at least one embodiment, the first processing unit 110, the second processing unit 210 and the third processing unit 310 can be a central processing unit, a digital signal processor, or a single chip, for example.

The driving safety controlling system 1 can include a number of modules, and the number of modules can include a matching module 11, an obtaining module 12, a submitting module 13, a transmitting module 14, a determining module 15 and a prompting module 16. The number of modules can be stored in the first storage unit 140, and/or second storage unit 230, and/or the third storage unit 330, and further applied on the first processing unit 110, and/or the second processing unit 210, and/or the third processing unit 310. In this embodiment, the allocation module 10, the first transmit control module 12, the calculating module 14, the matching module 11, the obtaining module 12 and the submitting module 13 can be stored in the first storage unit 140, and applied on the first processing unit 110. The transmitting module 14 can be stored in the second storage unit 230, and applied on the second processing unit 210. The determining module 15 and the prompting module 16 can be stored in the third storage unit 330, and applied on the third processing unit 310. The details are as follows.

The matching module 11 can be used to control the first communication unit 130 of the wearable device 100 to match with the second communication unit 220 of the smart key 200, such that the wearable device 100 can communicate with the smart key 200.

The obtaining module 12 can be used to obtain the sensing data, and the sensing data can include but not limited to a user's blood pressure, pulse rate, blink response, the number of eye-rolling or the like.

The submitting module 13 can be used to submit the sensing data to the smart key 200. The second communication unit 220 of the smart key 200 can receive the sensing data.

The transmitting module 14 can be used to obtain the unique identifier from the second storage unit 230, and further control the first wireless communication unit 240 to transmit a high-frequency signal containing the unique identifier and the sensing data.

When the vehicle 300 is within a predefined distance of the smart key 200, the second wireless communication unit 320 of the vehicle 300 can receive the high-frequency signal.

The determining module 15 can be used to obtain the unique identifier and the sensing data from the high-frequency signal, and obtain the predefined identifier and the range from the third storage unit 330, and compare the unique identifier with the predefined identifier, and further compare the sensing data with the range, if the unique identifier is matched with the predefined identifier and the sensing data is within the range, it is indicated that the user is in a normal state, if the unique identifier is matched with the predefined identifier, but the sensing data is not within the range, it is indicated that the user is in an abnormal state.

In detail, the determining module 15 can be used to obtain the unique identifier and the sensing data from the high-frequency signal, and further obtain the predefined identifier from the third storage unit 330, and compare the unique identifier with the predefined identifier, and determine whether the unique identifier is matched with the predefined identifier, and do not process the sensing data when determined that the unique identifier is not matched with the predefined identifier, and obtain the range from the third storage unit 330 when determined that the unique identifier is matched with the predefined identifier, and further compare the sensing data with the range; and determine whether the sensing data is within the range, and if the sensing data is within the range, it is indicated that the user is in a normal state, and if the sensing data is not within the range, it is indicated that the user is in an abnormal state.

The prompting module 16 can be used to control the prompt unit 340 to generate a prompting when determined that the unique identifier is matched with the predefined identifier and the sensing data is within the range. In at least one embodiment, the prompting can be but not limited to alarm prompting, voice prompting, light prompting or the like.

After the prompt unit 340 has prompted predefined time duration, if there is still no response, the vehicle 300 would be stopped, such that fatigue driving, drunk driving or the like can be avoided effectively.

Figure 3:
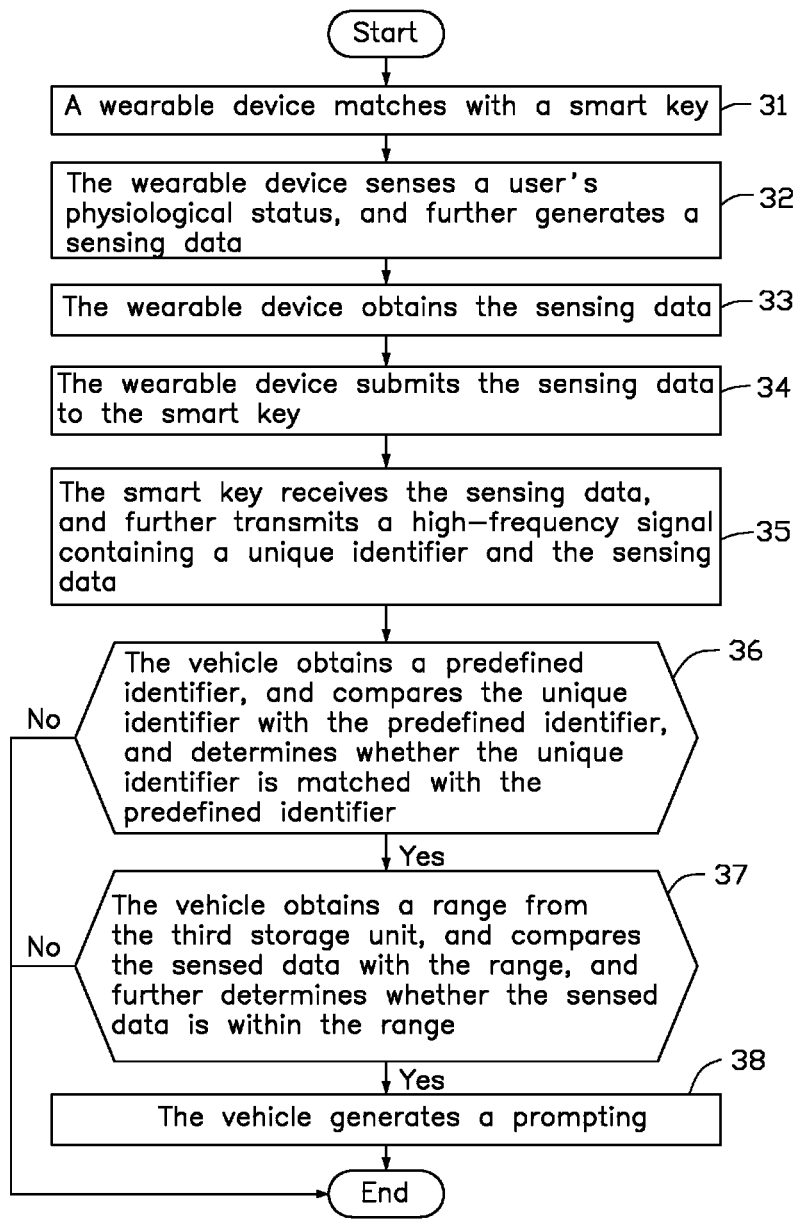
FIG. 3 is a flowchart of an embodiment of a driving safety controlling method.

FIG. 3 illustrates a flowchart of a driving safety controlling method. The control controlling method is provided by way of example, as there are a variety of ways to carry out the controlling method. The control controlling method described below can be carried out using the configurations illustrated in FIG. 1, for example, and various elements of these figures are referenced in explaining the example controlling method. Each block shown in FIG. 3 represents one or more processes, controlling methods, or subroutines carried out in the example controlling method. Furthermore, the illustrated order of blocks is by example only and the order of the blocks can be changed. Additional blocks may be added or fewer blocks may be utilized, without departing from this disclosure. The example controlling method can begin at block 31.

At block 31, a wearable device matches with a smart key. In detail, a matching module controls a first communication unit of the wearable device to match with a second communication unit of the smart key.

At block 32, the wearable device senses a user's physiological status, and further generates a sensing data. In detail, a sense unit senses a user's physiological status such as blood pressure, pulse rate, blink response, the number of eye-rolling or the like, and further generate the sensing data.

At block 33, the wearable device obtains the sensing data. In detail, an obtaining module obtains the sensing data.

At block 34, the wearable device submits the sensing data to the smart key. In detail, a submitting module controls a first communication unit of the wearable device to submit the sensing data to the smart key.

At block 35, the smart key receives the sensing data, and further transmits a high-frequency signal containing a unique identifier and the sensing data. In detail, the second communication unit of the smart key receives the sensing data, and an transmitting module obtains the unique identifier from a second storage unit of the smart key, and further controls a first wireless communication unit to transmit a high-frequency signal containing the unique identifier and the sensing data. When the vehicle is within a predefined distance of the smart key, a second wireless communication unit of the vehicle receives the high-frequency signal.

At block 36, the vehicle obtains a predefined identifier, and compares the unique identifier with the predefined identifier, and determines whether the unique identifier is matched with the predefined identifier, if yes, the process goes to block 37, otherwise, the process goes to end. In this embodiment, a determining module obtains the unique identifier and the sensing data from the high-frequency signal, and obtains the predefined identifier from a third storage unit, and compares the unique identifier with the predefined identifier, and determines whether the unique identifier is matched with the predefined identifier, if yes, the process goes to block 37, otherwise, the process goes to end.

At block 37, the vehicle obtains a range from the third storage unit, and further compares the sensing data with the range; and determines whether the sensing data is within the range, if yes, the process goes to block 38, otherwise, the process goes to end. In this embodiment, the determining module obtains the range from the third storage unit, and further compares the sensing data with the range; and determines whether the sensing data is within the range, if yes, the process goes to block 38, otherwise, the process goes to end.

At block 38, the vehicle generates a prompting. In detail, a prompting module controls a prompt unit to generate a prompting.

In at least one embodiment, the first wireless communication unit 240 and the second communication unit 320 can communicate with each other by transmitting a low-frequency signal and receiving a low-frequency signal.

In at least one embodiment, the first wireless communication unit 240 and the second wireless communication unit 320 can communicate with each other by transmitting a low-frequency signal or a high-frequency signal, and receiving a low-frequency signal or a high-frequency signal.

In at least one embodiment, for descriptive simplification, the low-frequency signal and the high-frequency signal can be both called communication signal.

In at least one embodiment, the "match" can be that the predefined identifier is same with the unique identifier, or the predefined identifier is only corresponded to the unique identifier.

The embodiments shown and described above are only examples. Many details are often found in the art. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A driving safety controlling system, running on a wearable device, a smart key and a vehicle, the driving safety controlling system comprising:
    a plurality of processors; and
    a plurality of non-transitory computer readable mediums, coupled to the plurality of processors and configured to store instructions for execution by the plurality of processors, the instructions causing the plurality of processors to:
        obtain sensing data from the wearable device, wherein the sensing data is generated by the wearable device via sensing a user's physiological status;
        submit the sensing data to the smart key;
        obtain a unique identifier from the smart key and control the smart key to transmit a high-frequency signal containing the unique identifier and the sensing data to the vehicle;
        obtain the unique identifier and the sensing data from the high-frequency signal;
        obtain a predefined identifier and a range from the vehicle;
        compare the unique identifier with the predefined identifier;
        compare the sensing data with the range; and
        control the vehicle to generate a prompting when the unique identifier is determined to match the predefined identifier and the sensing data is within the range.

2. The driving safety controlling system of claim 1, wherein the instructions causes the plurality of processors to prevent the vehicle from processing any sensing data when the unique identifier is not determined to match the predefined identifier.

3. The driving safety controlling system of claim 1, wherein the instructions causes the plurality of processors to prevent the vehicle from generating the prompting when the unique identifier is determined to match the predefined identifier but the sensing data is not within the range.

4. The driving safety controlling system of claim 1, wherein the prompting can be selected from a group consisting of alarm prompting, voice prompting and light prompting.

5. The driving safety controlling system of claim 1, wherein the instructions causes the plurality of processors to match the wearable device with the smart key.

6. A driving safety controlling method, running on a wearable device, a smart key and a vehicle, the driving safety controlling method comprising:
    obtaining sensing data from the wearable device, wherein the sensing data is generated by the wearable device via sensing a user's physiological status;
    submitting the sensing data to the smart key;
    obtaining a unique identifier from the smart key;
    controlling the smart key to transmit a high-frequency signal containing the unique identifier and the sensing data to the vehicle;
    obtaining the unique identifier and the sensing data from the high-frequency signal, obtaining a predefined identifier and a range from the vehicle;
    comparing the unique identifier with the predefined identifier;
    comparing the sensing data with the range; and
    controlling the vehicle to generate a prompting when the unique identifier is determined to match with the predefined identifier and the sensing data is within the range.

7. The driving safety controlling method of claim 6, wherein the driving safety controlling method further comprises:
    preventing the vehicle from processing any sensing data when the unique identifier is not determined to match the predefined identifier.

8. The driving safety controlling method of claim 6, wherein the driving safety controlling method further comprises:
    preventing the vehicle from generating the prompting when the unique identifier is determined to matched the predefined identifier but the sensing data is not within the range.

9. The driving safety controlling method of claim 6, wherein the prompting can be selected from a group consisting of alarm prompting, voice prompting and light prompting.

10. The driving safety controlling method of claim 6, wherein the driving safety controlling method further comprises:
    matching the wearable device with the smart key.

* * * * *